United States Patent [19]
Stahurski

[11] Patent Number: 5,304,178
[45] Date of Patent: Apr. 19, 1994

[54] SUBLAMINAR WIRE

[75] Inventor: Terrence Stahurski, Rocky River, Ohio

[73] Assignee: AcroMed Corporation, Cleveland, Ohio

[21] Appl. No.: 889,818

[22] Filed: May 29, 1992

[51] Int. Cl.$^5$ .................. A61B 17/56; A61B 17/58
[52] U.S. Cl. ............................ 606/61; 606/72
[58] Field of Search .......... 24/129 C, 131 R, 908, 24/27, 29; 606/53, 60, 61, 69, 72, 73, 74, 86, 103; 128/69

[56] References Cited

U.S. PATENT DOCUMENTS

| | | | |
|---|---|---|---|
| 1,237,034 | 8/1917 | Harris | 24/27 X |
| 1,419,110 | 6/1922 | Cary | 24/27 |
| 1,502,625 | 7/1924 | Gerrard et al. | 24/27 |
| 1,705,087 | 3/1929 | Gerrard et al. | 24/27 |
| 3,949,450 | 4/1976 | Bailey | 24/27 |
| 4,643,178 | 2/1987 | Nostari et al. | 606/74 |
| 4,738,251 | 4/1988 | Plaza | 606/61 |
| 4,998,936 | 3/1991 | Mehdian | 606/61 |
| 5,030,220 | 7/1991 | Howland | 606/73 X |
| 5,092,866 | 3/1992 | Bread et al. | 606/60 X |
| 5,092,868 | 3/1992 | Mehdian | 606/74 |
| 5,127,413 | 7/1992 | Ebert | 606/103 X |

Primary Examiner—Robert A. Hafer
Assistant Examiner—Brian E. Hanlon
Attorney, Agent, or Firm—Tarolli, Sundheim & Covell

[57] ABSTRACT

A sublaminar wire for connecting a spinal column corrective device to a spinal column has first and second end portions. A flat center portion extendable under the lamina of a vertebra of the spinal column has a larger cross-sectional area than each of the cross-sectional areas of the first and second end portions.

7 Claims, 2 Drawing Sheets 5,304,178

SUBLAMINAR WIRE

BACKGROUND OF THE INVENTION

The present invention relates to a new and improved sublaminar wire for connecting a spinal column corrective device to a spinal column. More specifically, the present invention relates to a sublaminar wire having a center portion positionable under the lamina of a vertebra of the spinal column and having a larger cross-sectional area than each of the cross-sectional areas of first and second end portions of the sublaminar wire.

A known sublaminar wire has the same circular cross-sectional area along its entire length. The cross-sectional area of the sublaminar wire is relatively small. As a result, the sublaminar wire may break at a portion of the sublaminar wire inside the spinal canal where it may engage the spinal cord and cause harm. The known sublaminar wire of relatively small cross section also may tear through the lamina of the vertebra releasing the spinal column corrective device from the spinal column.

SUMMARY OF THE INVENTION

The present invention is a new and improved sublaminar wire for connecting a spinal column corrective device to a spinal column. The sublaminar wire has first and second end portions interconnected by a center portion. The center portion is locatable under the lamina of the vertebra of the spinal column. The center portion has a larger cross-sectional area than the cross-sectional areas of each of the first and second end portions. The large cross-sectional area of the center portion minimizes the possibility of breakage of the center portion and the possibility of the sublaminar wire tearing through the lamina of the vertebra. If the sublaminar wire breaks, it tends to break along the first or second end portion and not in the center portion which is in the spinal canal.

BRIEF DESCRIPTION OF THE DRAWINGS

Further features of the present invention will become apparent to those skilled in the art to which the present invention relates from reading the following specification with reference to the accompanying drawings, in which.

DESCRIPTION OF A PREFERRED EMBODIMENT

A pair of surgically implantable rods, (FIG. 1) for correcting deformation of a spinal column C are connected with several vertebrae V of the spinal column. Clamps 22, hooks 24 and sublaminar wires 28, embodying the present invention connect the rods 20 with the vertebrae. The clamps 22 and the hooks 24 are well known in the art and may be similar to the clamps and hooks of U.S. Pat. No. 5,024,213 which is assigned to the assignee of the present invention.

Figures 1, 2:
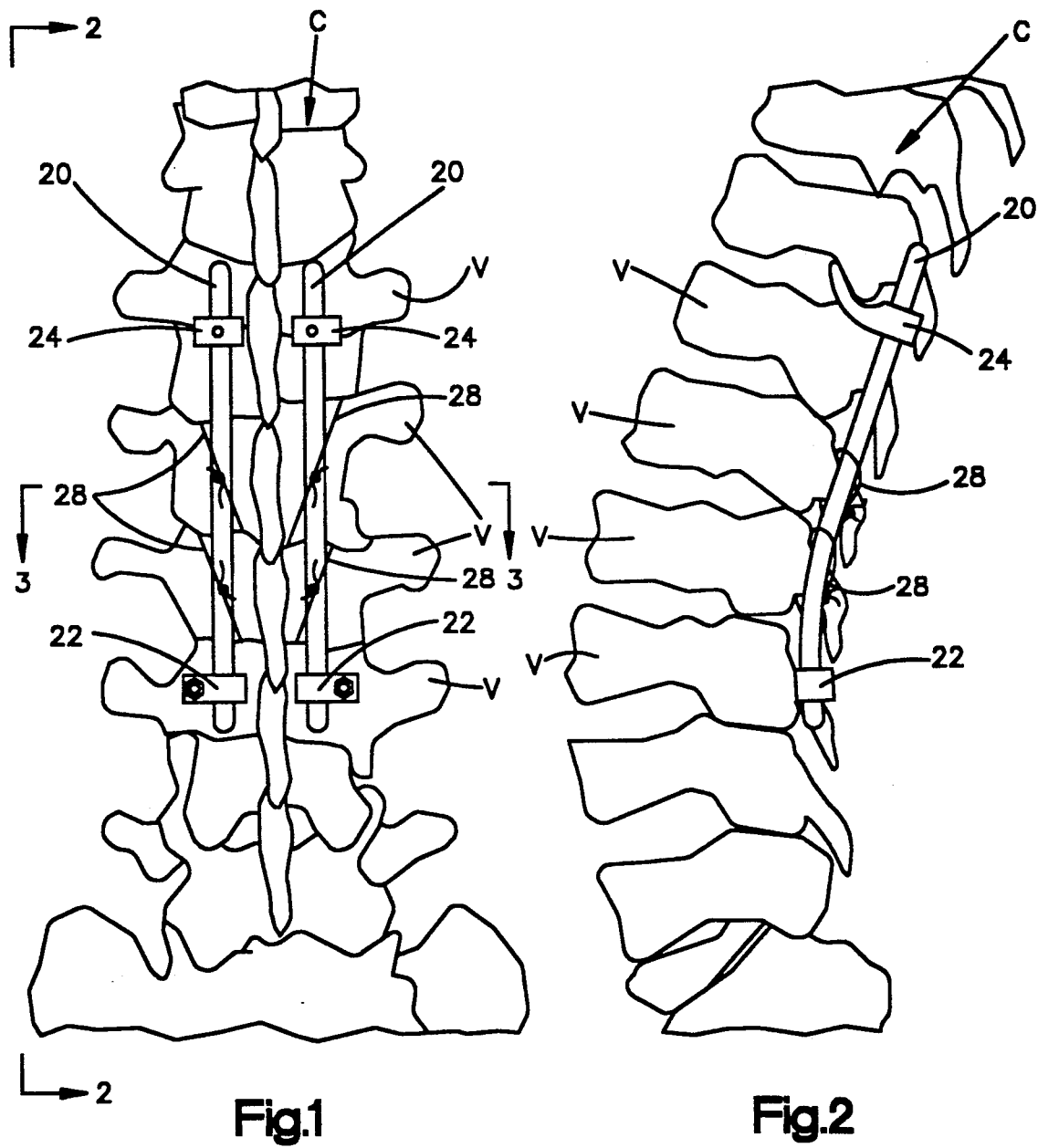
FIG. 1 is a view of a corrective device connected with a portion of a human spinal column by sublaminar wires embodying the present invention.
FIG. 2 is a view taken along the line 2—2 of FIG. 1.

Each rod 20 is elongate and has a circular cross-section taken in a plane extending perpendicular to longitudinal central axis of the rod. The rod 20 is bendable in any desired plane to conform to a desired curvature of the spinal column C, as illustrated in FIG. 2. The rod 20 has sufficient strength and rigidity to maintain the vertebrae V in the desired relationship.

Figure 4:
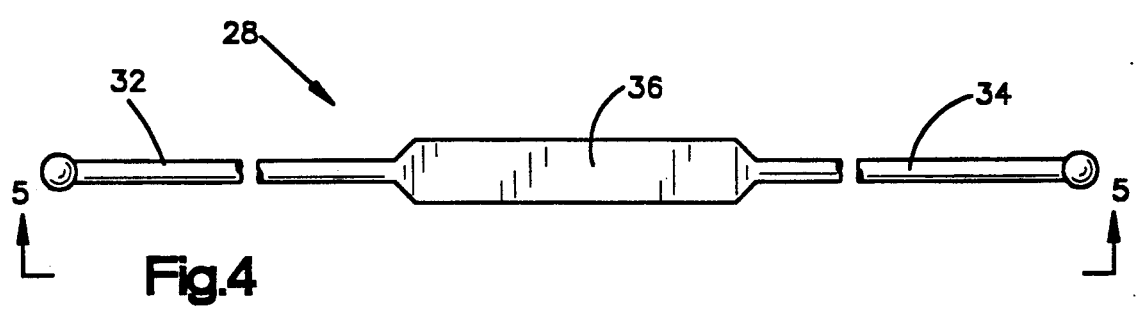
FIG. 4 is a plan view of a sublaminar wire of the present invention.

Each of the sublaminar wires 28 (FIGS. 4 and 5) has end portions 32 and 34 interconnected by a center portion 36. Preferably the center portion 36 and end portions 32 and 34 are formed from a homogenous single piece of material, but could be formed with a center piece crimped to a wire extending through a passage in the center piece. The sublaminar wire 28 is made of stainless steel or any other suitable bendable biocompatible material. The overall length of the sublaminar wire 28 is about eight to twelve inches.

Figure 3:
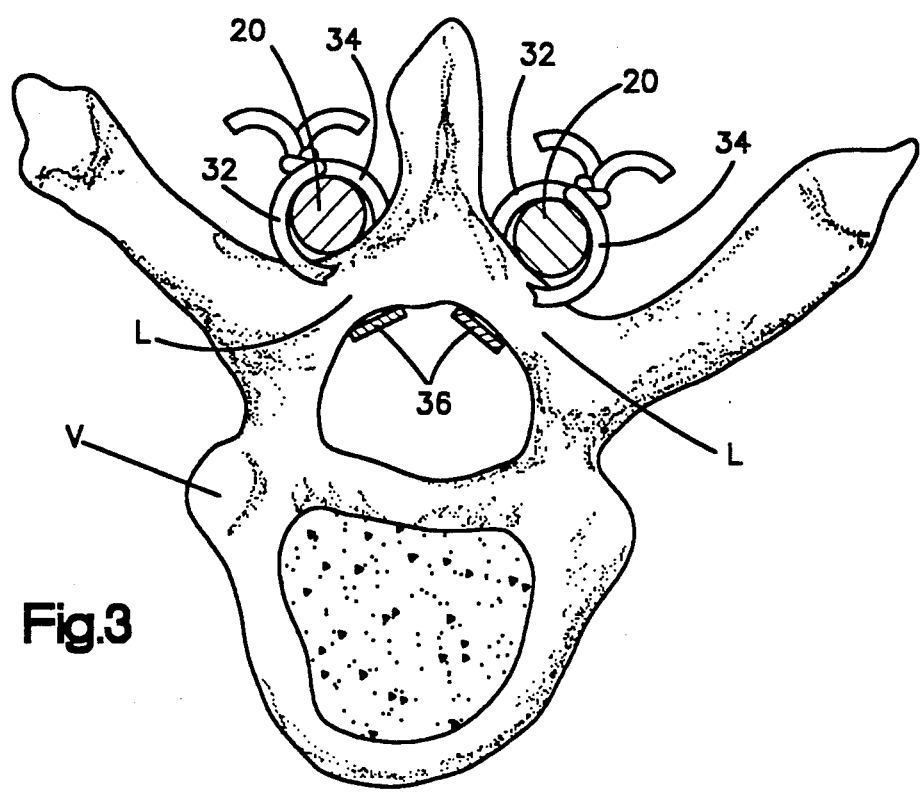
FIG. 3 is a view taken along the line 3—3 of FIG. 1.

The end portions 32 and 34 have circular cross-sections. The center portion 36 has a rectangular cross-section (FIG. 3). The rectangular cross-sectional area of the center portion 36 is larger than the cross-sectional areas of each of the end portions 32 and 34.

Figure 5:
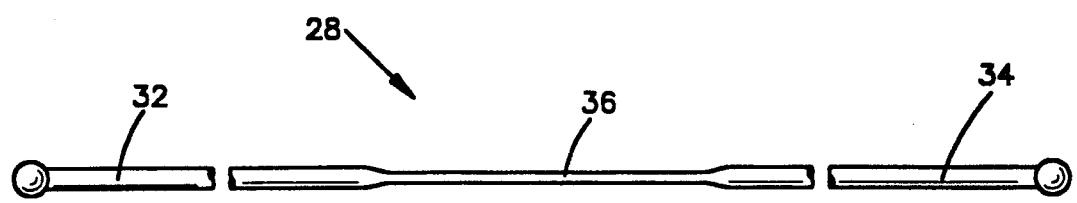
FIG. 5 is a view taken along the line 5—5 of FIG. 4.

The center portion 36 has a thickness that is less than the diameter of the first and second end portions (FIG. 5). The width of the center portion 36 is preferably between two to five times the diameter of the first and second end portions. The length of the center portion 36 may vary from about one-half of an inch for use in a child to about two inches for use in an adult.

To connect the rods 20 to the vertebrae V, the sublaminar wire 28 is inserted under the lamina L of the vertebrae V (FIG. 3). The center portion 36 engages the lamina of the vertebra and the end portions 32 and 34 are twisted about the rod 20 to connect the rod to the vertebra V. Any excess wire is trimmed off. Thus, the center portion 36 with the large cross-sectional area is located in the spinal canal of the vertebra V.

From the above description of the invention, those skilled in the art will perceive improvements, changes and modifications. Such improvements, changes and modifications within the skill of the art are intended to be covered by the appended claims.

I claim:

1. An apparatus for use in retaining spinal elements in a desired spatial relationship comprising:

a longitudinal member positionable along the spinal column; and a sublaminar wire having first and second end portions extending around and engaging at least a portion of said longitudinal member, each of said first and second end portions having a circular cross-section lying in a plane extending perpendicular to the longitudinal axis of said sublaminar wire and a center portion interconnecting said first and second end portions and adapted for engaging a lamina of the spinal column, said center portion being an elongated flat planar member having a rectangular cross-section lying in a plane extending perpendicular to the longitudinal axis of said sublaminar wire and a larger cross-sectional area than each of the cross-sectional areas of said first and second end portions;

said center portion including first and second major side surfaces substantially parallel to each other and first and second minor side surfaces interconnecting said first and second major side surfaces, said first and second major side surfaces being spaced apart by a first distance, said first and second minor side surfaces being spaced apart by a second distance, said first distance being smaller than said second distance, a substantial length of one of said first and second major side surfaces adapted for engaging the lamina of the spinal column.

2. A sublaminar wire as set forth in claim 1 wherein the thickness of said center portion is less than the diameter of said first and second end portions.

3. A sublaminar wire as set forth in claim 2 wherein the width of said center portion is substantially between 2 to 5 times the diameter of said first and second end portions.

4. A sublaminar wire as set forth in claim 1 wherein said first and second end portions and said center portion are formed from a continuous piece of wire.

5. An apparatus as set forth in claim 1 wherein said apparatus includes a plurality of sublaminar wires, each of said sublaminar wires having a center portion with a larger cross-sectional area than each of the cross-sectional areas of first and second end portions.

6. An apparatus as set forth in claim 5 further including clamps connecting said longitudinal member to the spinal column.

7. An apparatus as set forth in claim 1 further including hooks connecting said longitudinal member to the spinal column.

* * * * *